(12) United States Patent
Vodyanoy et al.

(10) Patent No.: US 7,551,349 B2
(45) Date of Patent: Jun. 23, 2009

(54) HIGH RESOLUTION OPTICAL MICROSCOPE WITH CARDIOID CONDENSER FOR BRIGHTFIELD AND DARKFIELD ILLUMINATION

(75) Inventors: Vitaly Vodyanoy, Auburn, AL (US); Arnold Vainrub, Auburn, AL (US); Oleg Pustovyy, Auburn, AL (US)

(73) Assignee: Auburn University, Auburn, AL (US)

( * ) Notice: Subject to any disclaimer, the term of this patent is extended or adjusted under 35 U.S.C. 154(b) by 396 days.

(21) Appl. No.: 11/607,369

(22) Filed: Dec. 1, 2006

(65) Prior Publication Data

US 2007/0127117 A1     Jun. 7, 2007

Related U.S. Application Data

(60) Provisional application No. 60/741,508, filed on Dec. 1, 2005.

(51) Int. Cl.
    *G02B 21/06* (2006.01)
(52) U.S. Cl. ........................................... 359/385
(58) Field of Classification Search .......... 359/385–390
    See application file for complete search history.

(56) References Cited

U.S. PATENT DOCUMENTS

| | | | |
|---|---|---|---|
| 1,544,973 A | | 7/1925 | Ghadiali |
| 1,613,583 A | * | 1/1927 | Berek .......................... 359/387 |
| 1,943,510 A | * | 1/1934 | Bauersfeld et al. .......... 359/387 |
| 1,951,636 A | | 3/1934 | Straubel |
| 1,996,920 A | | 4/1935 | Hauser |
| 2,129,562 A | * | 9/1938 | Brueck ........................ 396/510 |
| 2,130,494 A | * | 9/1938 | Heine .......................... 359/799 |
| 2,642,775 A | * | 6/1953 | Rooney ....................... 359/387 |
| 2,674,157 A | | 4/1954 | Heine ............................. 88/39 |
| 3,666,362 A | | 5/1972 | Chance ......................... 356/88 |
| 3,930,713 A | * | 1/1976 | Stankewitz et al. .......... 359/387 |
| 4,109,304 A | * | 8/1978 | Khvalovsky et al. ......... 362/259 |
| 4,246,488 A | | 1/1981 | Hura ........................... 250/513 |
| 4,317,613 A | * | 3/1982 | Grosser ....................... 359/370 |
| 4,687,304 A | * | 8/1987 | Piller et al. .................. 359/387 |
| 4,894,760 A | | 1/1990 | Callahan ...................... 362/293 |

(Continued)

FOREIGN PATENT DOCUMENTS

CN          87 1 06138 A       10/1988

(Continued)

OTHER PUBLICATIONS

George E. Cragg et al., "Lateral Resolution Enhancement with Standing Evanescent Waves", Jan. 1, 2000, pp. 46-48, Optics Letters, Optical Society of America.

(Continued)

*Primary Examiner*—Alessandro Amari
*Assistant Examiner*—Mark Consilvio
(74) *Attorney, Agent, or Firm*—Haverstock & Owens LLP (57) ABSTRACT

The present invention is an improved illumination system which achieves enhanced spatial resolution and contrast in the observation of small objects. The enhanced performance is achieved by using a metal-halide light source, a power conservative pre-condenser optics train, an annular diaphragm, a cardioid annular condenser, and an adjustable light-filtering iris. These features are also intended to be used with a direct-view light optical microscope. A method of manufacturing and using the improved illumination system is also disclosed.

29 Claims, 6 Drawing Sheets

U.S. PATENT DOCUMENTS

| | | | |
|---|---|---|---|
| 4,974,094 A | 11/1990 | Morito | 358/225 |
| 5,113,332 A | 5/1992 | Richardson | 362/282 |
| 5,325,231 A * | 6/1994 | Tamura et al. | 359/387 |
| 5,394,268 A | 2/1995 | Lanni et al. | 359/386 |
| 5,400,135 A | 3/1995 | Maeda | 356/237 |
| 5,452,054 A | 9/1995 | Dewa et al. | 355/67 |
| 5,734,498 A * | 3/1998 | Krasieva et al. | 359/387 |
| 5,820,250 A | 10/1998 | Betts et al. | 362/216 |
| 5,841,577 A | 11/1998 | Wachman et al. | 359/386 |
| 6,002,484 A * | 12/1999 | Rozema et al. | 356/515 |
| 6,004,001 A | 12/1999 | Noll | 362/30 |
| 6,101,037 A | 8/2000 | Park et al. | 359/618 |
| 6,181,471 B1 | 1/2001 | Miyoshi | 359/388 |
| 6,597,499 B2 * | 7/2003 | Kawano et al. | 359/387 |
| 6,628,385 B1 | 9/2003 | Osipchuk et al. | 356/318 |
| 6,633,375 B1 * | 10/2003 | Veith et al. | 356/237.4 |
| 6,690,509 B2 | 2/2004 | Vodyanoy et al. | 359/368 |
| 6,704,140 B1 | 3/2004 | Richardson | 359/387 |
| 6,755,555 B2 | 6/2004 | Bloom et al. | 362/293 |
| 6,812,446 B2 | 11/2004 | Kreh | 250/201.3 |
| 6,839,166 B2 | 1/2005 | Fukushima et al. | 359/368 |
| 6,865,013 B2 | 3/2005 | Vodyanoy et al. | 359/305 |
| 6,947,127 B2 | 9/2005 | Wolleschensky et al. | 356/73 |
| 2001/0003489 A1 * | 6/2001 | Shiba et al. | 359/383 |
| 2002/0088952 A1 | 7/2002 | Rao et al. | 250/559.45 |
| 2002/0135871 A1 * | 9/2002 | Vodyanoy et al. | 359/389 |
| 2003/0086163 A1 | 5/2003 | Aono et al. | 359/388 |
| 2004/0239797 A1 | 12/2004 | Masuda | 348/362 |
| 2004/0258405 A1 | 12/2004 | Shiratori et al. | 396/458 |
| 2004/0262529 A1 | 12/2004 | Yoshida et al. | 250/372 |
| 2005/0237605 A1 * | 10/2005 | Vodyanoy et al. | 359/385 |
| 2005/0238347 A1 | 10/2005 | Oh | 396/449 |
| 2006/0001973 A1 | 1/2006 | Peterson et al. | 359/618 |
| 2006/0023301 A1 * | 2/2006 | Dietrich et al. | 359/387 |
| 2007/0014002 A1 * | 1/2007 | Vodyanoy et al. | 359/387 |
| 2007/0041109 A1 * | 2/2007 | Brehm et al. | 359/857 |
| 2007/0242336 A1 * | 10/2007 | Vodyanoy et al. | 359/234 |

FOREIGN PATENT DOCUMENTS

| | | |
|---|---|---|
| DE | 31 00 662 A1 | 12/1981 |
| EP | 0 504 940 A2 | 9/1992 |
| JP | 5-346532 | 12/1993 |
| JP | 2002-202459 A | 7/2002 |

OTHER PUBLICATIONS

Vitaly Vodyanoy, "High Resolution Light Microscopy of Live Cells", May 2005, pp. 26-28 & 17, Microscopy Today.

Xiaolin Nan et al., "Lights up Lipids in Living Cells", Reprinted from the Aug. 2004 issue of Biophotonics International, pp. 1-4, CARS Microscopy, Live Cell Imaging, A Laurin Publication Biophotonics International.

Prof.Dr.Phil. J. Eisenbrand, Priv.Doz.Dr.Med.G.Werth, "Fluoreszenz-Mikroskopie", Leipzig 1959, Akademische Verlagsgesellschaft Geest & Protig K.-G.

Ji-Xin Cheng and X. Sunney Xie, "Coherent Anti-Stokes Raman Scattering Microscopy: Instrumentation, Theory, and Applications", Jun. 14, 2003; In Final Form: Oct. 2, 2003, published on the web Dec. 25, 2003, pp. 827-840, J. Phys. Chem. B 2004, Department of Chemistry and Chemical Biology, Harvard University, 12 Oxford Street, Cambridge, Massachusetts 02138.

Mathias Flörsheimer, Christof Brillert, and Harold Fuchs, "Chemical Imaging of Interfaces by Sum Frequency Microscopy", Received Nov. 5, 1998. In final From Jan. 14, 1999 Langmuir 1999, Published on the web Feb. 24, 1999, pp. 5437-5439, Physical Institute, University of Münster, Wilhelm-Klemm-Strasse 10, D-48149 Münster, Germany.

Lord Rayleigh, Sec. R.S., "XV. On the Theory of Optical Images, with Special Reference to the Microscope", 1896, vol. XLII, pp. 167-195, Lord Rayleigh, Philosophical Magazine.

Maksymilian Pluta, "Advanced Light Microscopy", 1989, pp. 211-216 vol. 2, Elsevier Amsterdam-Oxford-New York-Tokyo PWN-Polish Scientific Publishers, Warszawa.

Arnold Vinrub, Oleg Pustovyy, and Vitaly Vodyanoy, "Resolution of 90 nm 1/5) in an optical transmission microscope with an annular condenser", Received Jun. 12, 2006, posted Jul. 16, 2006, (Doc ID 71923) Published Sep. 11, 2006, Oct. 1, 2006, vol. 31 No. 19, pp. 2855-2857, Department of Anatomy, Physiology and Pharmacology, College of Veterinary Medicine, Auburn University, Auburn, Alabama 36849.

JiXin Cheng, Y. Kevin Jia, Gengfeng Zheng, and X. Sunney Xie, "Laser-Scanning Coherent Anti-Stokes Raman Scattering Microscopy and Applications to Cell Biology", Jul. 2002, vol. 83, pp. 502-509, Department of Chemistry and Chemical Biology, Harvard Univeristy, Cambridge, Massachusetts 02138, and SEG, Olympus America Inc., Biophysical Journal Department, Melville, New York 11747-3157 USA.

Barbara Foster, "Focus on Microscopy: A Technique for Imaging Live Cell Interactions and Mechanisms", Nov. 2004, Reprinted from American Laboratory, 5 pages.

* cited by examiner

HIGH RESOLUTION OPTICAL MICROSCOPE WITH CARDIOID CONDENSER FOR BRIGHTFIELD AND DARKFIELD ILLUMINATION

RELATED APPLICATIONS

The present application claims priority to U.S. Provisional Patent Application 60/741,508, filed on Dec. 1, 2005, and entitled "High Resolution Optical Microscope" to the same inventor under U.S.C. section 119(e). This application incorporates U.S. Provisional Patent Application 60/741,508, filed on Dec. 1, 2005, and entitled "High Resolution Optical Microscope" to the same inventor by reference in its entirety.

FIELD OF THE INVENTION

The present invention relates generally to the field of optical microscopy. More particularly, the invention relates to optical microscopes with enhanced spatial resolution and contrast and a method of manufacturing and using the same.

BACKGROUND

All living creatures including humans are made of cells. The majority of life forms exist as single cells that perform all functions to continue independent life. A number of cells, cell organelles, bacteria and viruses are too small to be seen with traditional optical microscopes. To view cellular life, the microscope must have high resolution.

Resolution is the ability of a microscope to distinguish between two objects that are very close together. A microscope with a resolution of 1,000 Å (1,000 Angstroms; equal to 100 nanometers), for example, can make objects as close together as 100 nanometers independently visible. Objects and features smaller than 100 nanometers cannot be resolved (i.e., distinguished) by a microscope with a resolution of 1000 Å.

Currently there are a few microscopes which offer very fine resolution. One example is the "High-Resolution Optical Microscope" described in U.S. Pat. No. 6,690,509.

Electron microscopes are another example. However, in using electron microscopes, the specimen must be prepared by high-vacuum dehydration and is subjected to intense heat by the electron beam, making observation of living specimens impossible. The sample preparation for electron microscopy requires living cells to be killed, frozen, dehydrated and impregnated with heavy metals. The dehydration process also alters the specimen, leaving artifacts and cell damage that were not present in nature. These procedures, together with electron beam damage caused during the observation of the cells creates the possibility that some components of the cell may be lost or destroyed. Also, in order to view the steps in a biological process, dozens of specimens must be viewed at various stages in order to capture each desired step. Further, specimen preparation for electron microscopes can take up to two hours each.

The high cost of an electron microscope represents another barrier to its use in the life sciences. Electron microscopes are large and often require an entire room. The operation and adjustment of an electronic microscope also requires highly skilled technicians.

The ultraviolet microscope offers finer resolution and better magnification than an ordinary light microscope, but it has serious disadvantages for the study of living specimens. Ultraviolet light damages or kills many kinds of living biological specimens, making observation impossible. In ultraviolet microscopy specimens are often stained with a fluorescent dye. Many fluorescent dyes bind strongly to elements such as enzymes within living cells, changing their qualities and significantly altering the cellular biochemistry. Other dyes produce too much fluorescence or absorb too much of the ultraviolet light to be useful.

Like electron microscopes, the operation of an ultraviolet microscope requires a great deal of skill. Because ultraviolet light damages the human eye, the image can only be observed by ultraviolet video cameras or specially-equipped still cameras. Also, the quartz optics required for ultraviolet microscopes are much more expensive than the glass components used in visible light microscopes.

The electron and ultraviolet microscopes available today do not offer a technique for observing living, unaltered biological specimens in real time. The damage from the electronic beam, from fixing, freezing, exposure to ultraviolet light, and other procedures which occur during observation limits the processes which can be seen by such devices. For example, the phenomenon of cellular transport cannot be observed in non-living cells by these known devices. Other examples of phenomena which cannot be directly observed by electronic microscopes include: streaming, Brownian motion, diffusion, phagocytosis, pinocytosis, mitosis, immuno-fluorescence, and cell interactions.

It is important for scientists in the biomedical community to observe these living cells and their processes in order to better understand the cellular world. Currently, the behavior cells and the phenomena responsible can only be inferred. These processes can only be studied in depth while they are occurring and while the cells are alive. Observing live cellular activity is needed to more completely understand such processes as gene therapy, artificial insemination, new drug development, cell culturing and cloning, cell regeneration, implantation, bio-detection, and biotherapeutics, amongst others. Observing very small, live cells at a high resolution, with a high contrast could possibly lead to the development of treatments to diseases and other health problems.

SUMMARY OF THE DISCLOSURE

The present invention is an improved illumination system which achieves enhanced spatial resolution and contrast in the observation of small objects. Novel features of the invention include, but are not limited to the use of a metal-halide light source, a power conservative pre-condenser optics train, an annular diaphragm, a cardioid annular condenser, and an adjustable light-filtering iris. These features are also intended to be used with a direct-view light optical microscope.

The new illumination system for a direct-view light optical microscope allows increased resolution of cellular features, provides a unique view of live cells and cell processes while they are occurring, increases light economy which allows the use of a low power light source, enhances spatial resolution and contrast, lowers a microscope's detection limit, allows a magnifying power of more than 7,500 times, reduces stray light, and allows for three-dimensional sectioning capability. The illumination system for a direct-view light optical microscope does not produce image distortions and has a better resolution than current phase contrast microscopy techniques. The illumination system for a direct-view light optical microscope is adjustable and does not require a prerequisite orientation, as does current Differential Interference Contrast microscopy techniques. The illumination system for a direct-view light optical microscope is superior to conventional darkfield microscopy techniques due to better resolution, contrast, less heating, and reduced phototoxicity. Furthermore, the illumination system for a direct-view light optical microscope does not require that samples be prepared by freezing, staining, dehydration, labeling or metal deposition.

Enhanced resolution is achieved by minimizing the spot size incident on the sample and optimizing the point spread function of the light incident upon the sample specimen by creating optimal geometry based on theoretical calculations. The condenser used in the present invention directs an empty cone of light to a sample, the cone coming to a point with some "spot size". Minimizing the spot size increases the irradiance (energy per unit area) incident upon a sample. Increasing irradiance increases the contrast due to increased interaction with the smallest particles of the sample which would otherwise not be sufficiently excited to produce enough fluorescence light to be visible. Additionally, a small focal volume reduces a signal background and improves image contrast. Another benefit of a small focal volume is the capability of three-dimensional sectioning that may be used for reconstruction of three-dimensional images. Further, the point spread function of the light depends on the numerical aperture, or the angle the condenser emits light incident on the sample. In the present invention, an annular diaphragm is used to control the angle at which light is emitted from the condenser. Optimizing this angle will optimize resolution.

Reducing stray light and promotion of light economy enables more energy to be directed upon the sample allowing the system to be constructed with a less powerful and a cheaper light source. The reduction of stray light is accomplished a unique geometry that directs a cylinder of light to the condenser which corresponds to the circumference of the opening of the condenser. This configuration conserves light which enables the system to employ a less powerful and cheaper light. Further, the reduction of stray light limits undesirable heating in the system.

Theoretically, the resolution of a system depends on numerical aperture and the limit is characterized by Rayleigh's famous criteria: $R=0.61(\lambda/NA)$, where R is resolution, $\lambda$ is wavelength and NA is numerical aperture. The improved illumination system achieves a resolution better than $\lambda/5$, which surpasses 2.2 times the Rayleigh criteria. This occurs for two reasons: first the point spread function produced by the condenser is narrower, and second the diffraction fringes of the point spread function are strong with the condenser and the image shape is less convoluted.

In some embodiments of the invention the novel features listed above stand on their own to improve resolution and contrast. In other embodiments, the illumination system takes advantage of one or more of the novel features to accomplish synergic results.

BRIEF DESCRIPTION OF THE DRAWINGS

The novel features of the invention are set forth in the appended claims. However, for the purpose of explanation, several embodiments of the invention are set forth in the following figures.

DETAILED DESCRIPTION

The main function of a fluorescent microscope is to illuminate the sample with light of a specific wavelength (excitation light), excite a fluorescent light, and then separate the weak emitted fluorescent light from the excitation light. Fluorescence is a short time luminescence which is most commonly excited by light. When photons are directed toward a sample the energy in the photons causes the molecules in the sample to become excited. The excited state electron in the molecule jumps to the lowest energy level in the intermediate state and then goes through vibrational relaxation. Finally, the emission of a longer wavelength photon and recovery of the molecule into the ground state occurs.

Figure 1:
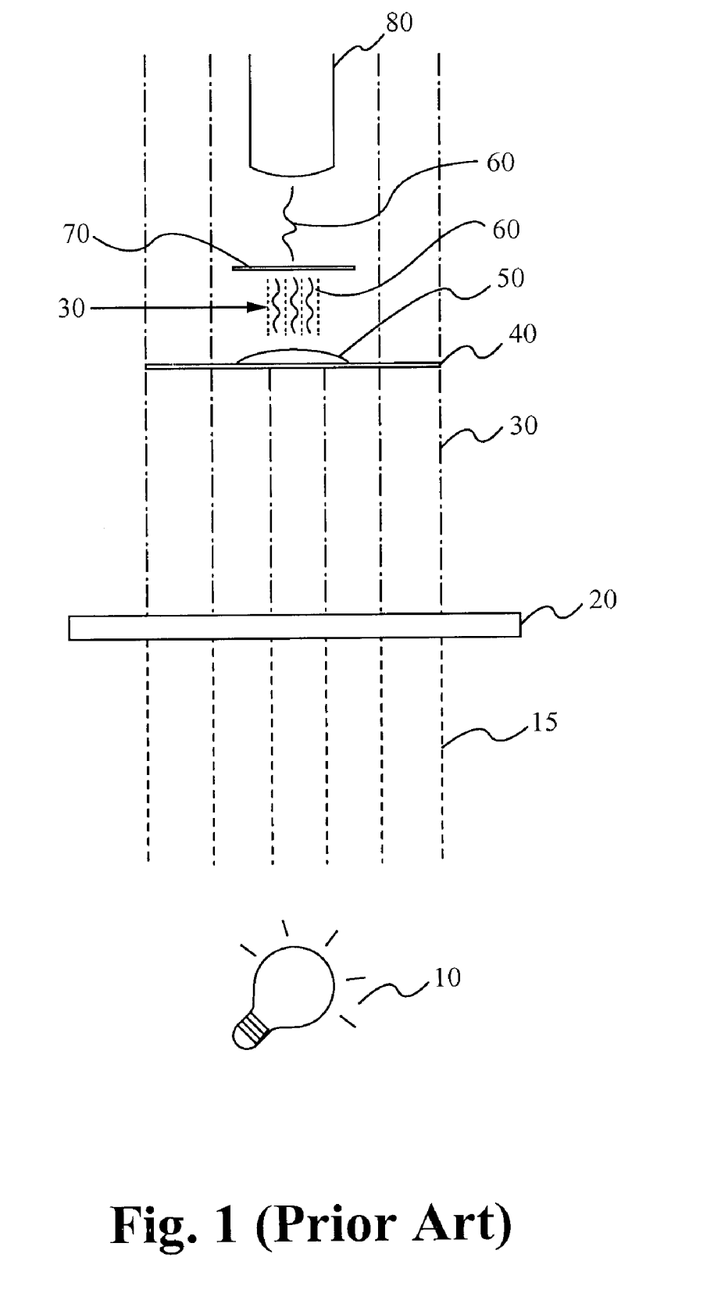
FIG. 1 illustrates the basic setup used in fluorescent microscopy.

FIG. 1 illustrates the basic setup used in fluorescent microscopy. A special light source 10 is used which emits light 15. A first filter 20 filters the light 15 from the light source 10 resulting in Excitation Light 30 with the proper wavelength to cause excitation in a specimen 50. This Excitation Light 30 is directed toward a slide 40 containing the specimen 50. The Excitation Light 30 incident on the specimen 50 excites molecules in the specimen resulting in emitted Fluorescent Light 60 with a higher wavelength. A portion of Excitation Light 30 also passes through the specimen unaltered. A second filter 70 is a Barrier Filter used to filter the Excitation Light 30 from the Fluorescent Light 60. The filtered Fluorescent Light 60 is then observed by an observation lens 80.

Figure 2:
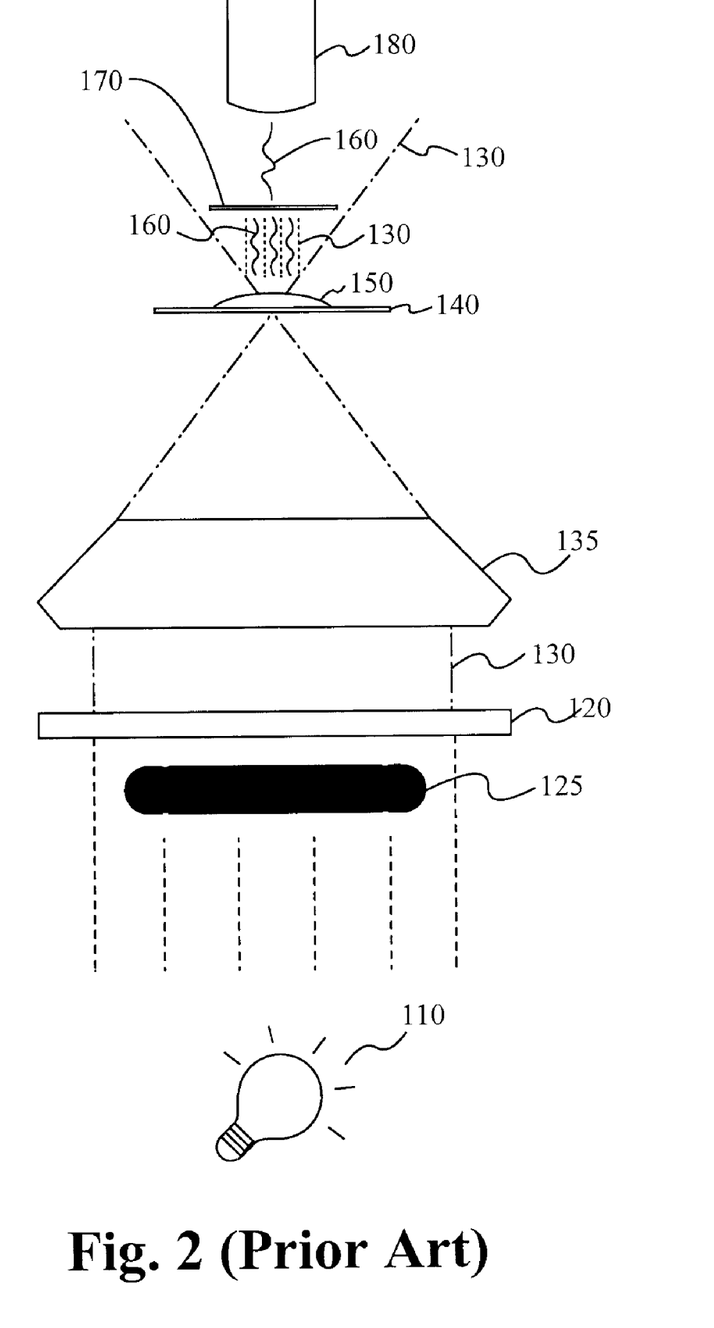
FIG. 2 illustrates the technique of Darkfield microscopy.

FIG. 2 illustrates the technique known as darkfield microscopy. Darkfield microscopy takes advantage of fluorescence to view small specimen, but uses a condenser 135 to direct the Excitation Light to some angle. Light from the light source 110 is directed toward a first filter 120, but before it reaches the filter 120, a portion of the light is blocked by an annular stop 125. The light which is not blocked forms a cylinder of light which continues to the first filter 120. The filter 120 blocks a portion of the light and allows only filtered light 130 to be directed to a Darkfield Condenser 135. The Darkfield Condenser 135 directs the light at some angle toward the slide 140 and the specimen 150. When the light enters the specimen 150 it causes fluorescence and Fluorescent Light 160 is emitted toward the observation lens. Most of the filtered light 130 continues at the same angle past the observation lens 180, but some light 130 leaves the specimen 150 with the same wavelength as the Excitation Light. A barrier filter 170 filters the Excitation Light out and only Fluorescent Light makes it to the observation lens. An image of the specimen appears to an observer in a dark field. This method of microscopy is effective, but is flawed in the following respects:

1. The numerical aperture of the objective lens needs to be reduced by a built-in iris diaphragm in order to prevent excitation light from entering the objective lens. This reduces the light intensity and resolution.
2. The Darkfield method is very wasteful of light since most of the light emitted from the source is blocked by the annular stop.
3. The darkfield condenser is difficult to align.
4. The emitted fluorescent light passes through the sample before reaching the objective lens and is therefore partially absorbed and scattered resulting in less intense images.

5. Conventional darkfield techniques preclude the use of simultaneous fluorescence viewing together with Phase Microscopy or Normarski Differential Interference Contrast Microscopy.

The present invention improves these methods and solves their shortcomings.

Figure 3:
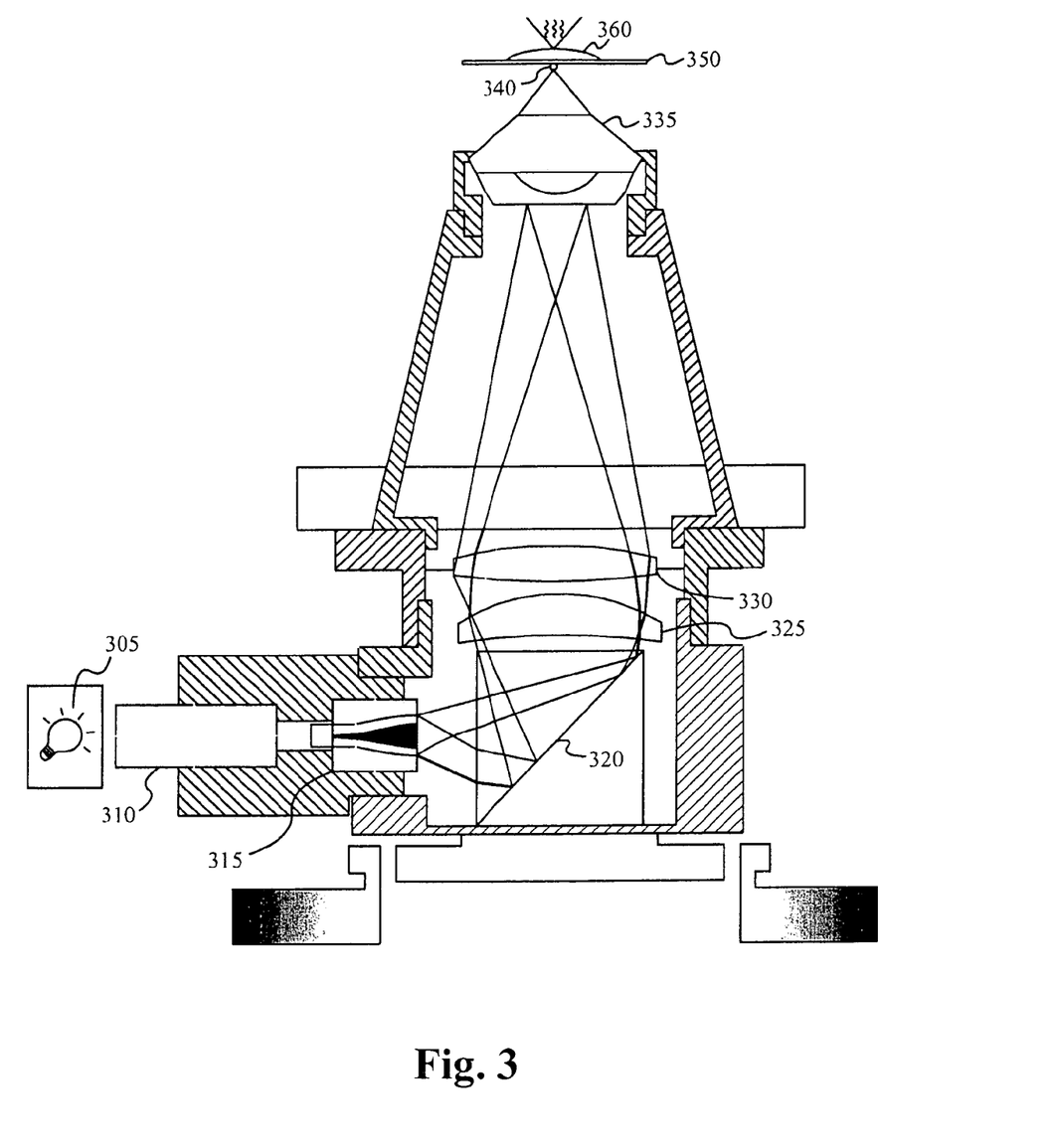
FIG. 3 is a side view of one embodiment of the present invention showing the enhanced illumination system.

FIG. 3 illustrates one embodiment of the advanced microscope illumination system of the present invention. Various aspects of the invention which are shown in FIG. 3 increase image resolution and contrast, either alone or in combination The first novel feature of the high definition illumination system 300 is a metal halide light-source 305. Unlike incandescent or halogen light sources that have a continuous spectrum of wavelengths, metal-halide lamps emit light that has few strong spectral lines with prominent peaks of intensity at 313, 334, 365, 406, 435, 546, and 578 nanometers. These few strong non-linear peaks interact with the sample to produce a high resolution and contrast. Two nonlinear phenomenon can be accounted to explain why an increase in resolution and contrast appear. The first is known as Coherent Anti-Stokes Raman Scattering (CARS). This is a nonlinear optical wave-mixing process. For CARS microscopy, two laser beams with two frequencies are spatially overlapped. When the frequency difference coincides with the frequency of a vibrational transition of the sample, a strong CARS signal is generated. The second nonlinear vibrational process is a Sum Frequency Generation (SFG). SFG is a nonlinear process requiring two incident laser beams focused to a common spot, generating a new frequency equal to the sum of the initial frequencies. This method provides vibrational contrast when one of the frequencies or the sum of the frequencies is on resonance with the molecular or electronic vibration of the sample.

Next, a collimating light adaptor 315 helps to increase resolution and light economy. Light from the metal-halide light source 305 is directed through a light guide 310 and is adjusted by a collimating light adaptor 315. The collimating light adaptor 315 shown in FIG. 3 is an axicone lens adaptor. The axicone lens adaptor 315 directs the light to a mirror 320. The mirror 320 directs the light through two prisms 325, 330 which focus an empty cylinder of light to the darkfield condenser 335. The darkfield condenser 335 only allows a cylinder of light to enter through a cylindrical slot (not shown). By using the axicone lens adaptor 315, the cylinder of light directed to the condenser 335 is the same size as the slot and a stop is not needed to block a portion of the light, thus greatly improving light economy. In some embodiments of the present invention, the metal-halide lamp 305 is powered by a 21 Watt power supply. For these reasons, the problems associated with the wasteful Darkfield method is solved by the present invention since the light emitted from the source is not blocked by the annular stop.

Finally, the geometry and configuration of the darkfield condenser 335 itself improves resolution and contrast. The darkfield condenser 335 focuses the light to a focal point 340 at the slide 350 where it interacts with specimen 360. As explained above, enhanced resolution achieved by the present invention is achieved by minimizing the spot size incident on the sample and optimizing the point spread function of the light incident upon the sample specimen 360 by angling the light based on theoretical calculations. As the condenser 335 directs light to a sample, the size of the cone can be adjusted to minimize its spot size. Minimizing the spot size increases the irradiance (energy per unit area) incident upon a sample. Increasing irradiance increases the contrast due to increased interaction with the smallest particles of the sample which would otherwise not be sufficiently excited to produce enough fluorescence light to be visible. FIGS. 4A, 4B, 5A and 5B illustrate how the condenser 335 is able to be adjusted.

Figure 4A:
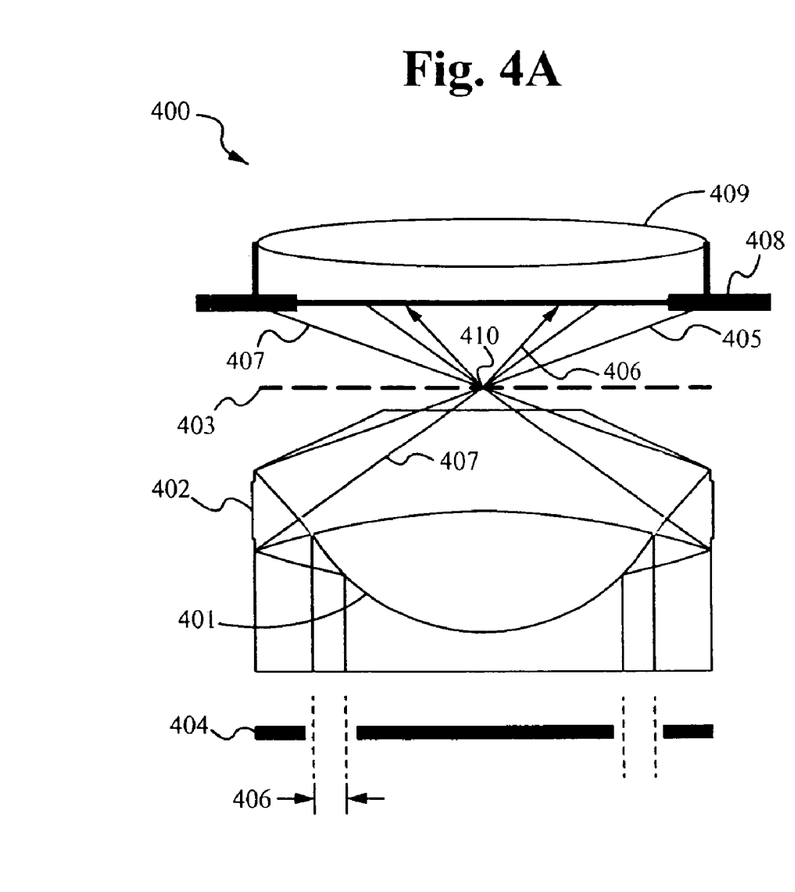
FIG. 4A is a view of the condenser with the annular diaphragm in a "narrow" position.

FIG. 4A illustrates one embodiment of the darkfield condenser of the present invention. A cylinder of light enters the condenser 400 through an annular diaphragm 404. The width of the cylinder has a thickness 406. The light then comes into contact with a spherical lens 401. The spherical lens 401 is specially designed to reflect the light at a certain angle. The light is again reflected on the inside Cardioid surface 402 and directed toward the top of the condenser 400. As the light exits the condenser 400, it comes to a focal point 410 near the slide 403. The focal point 410 can be aligned up and down based on what portion of a sample (not shown) is being excited. Once the light reaches its focus, it continues on as an inverted cone of light 405. Light produced as a result of fluorescence 406 is emitted from the sample. The emitted light 406 travels up and reaches an objective lens where it is observed. Finally, an iris 408 is adjustable to alternatively allow incident light 407 from reaching the objective lens 409.

Figure 4B:
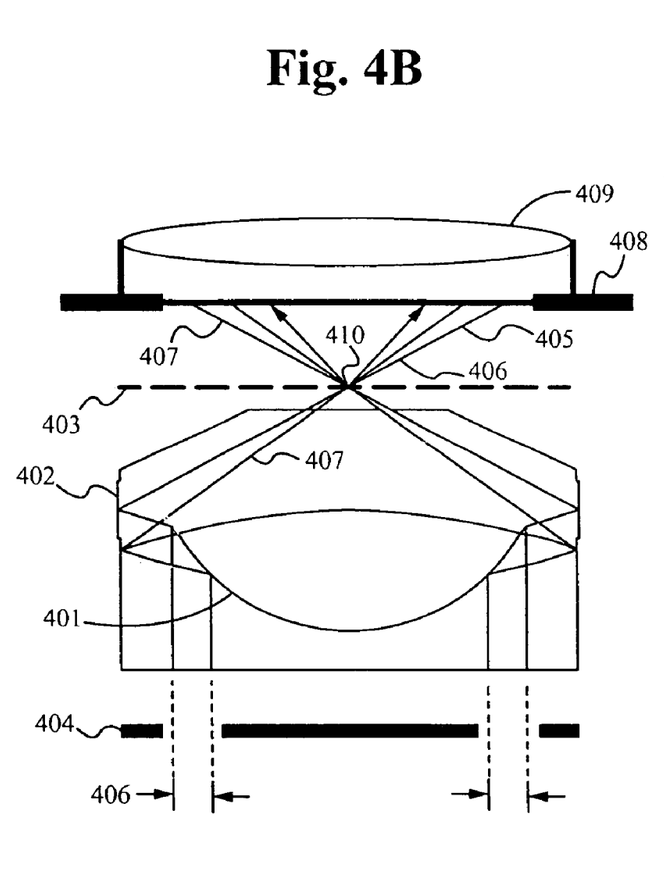
FIG. 4B is a view of the condenser with the annular diaphragm in a "broad" position.

FIG. 4B shows the same configuration as FIG. 4A, except that the annular diaphragm 404 is opened wider than in FIG. 4A. As shown, a wider cylinder of light enters the condenser 400. The spherical lens 401 reflects the light at a different angle creating a sharper focal point 410. Thus, opening and closing the annular diaphragm 404 adjusts the ability to use a high numerical aperture by changing the angle of incident light. This ability allows for high resolution which is better than $\lambda/5$, which surpasses 2.2 times the Rayleigh criteria. This occurs for two reasons: first the point spread function produced by the condenser is narrower, and second the diffraction fringes of the point spread function are strong with the condenser and the image shape is less convoluted. Optical conditions for high resolution are achieved with an aperture ranging from 1.25 to 1.43.

Figure 5A:
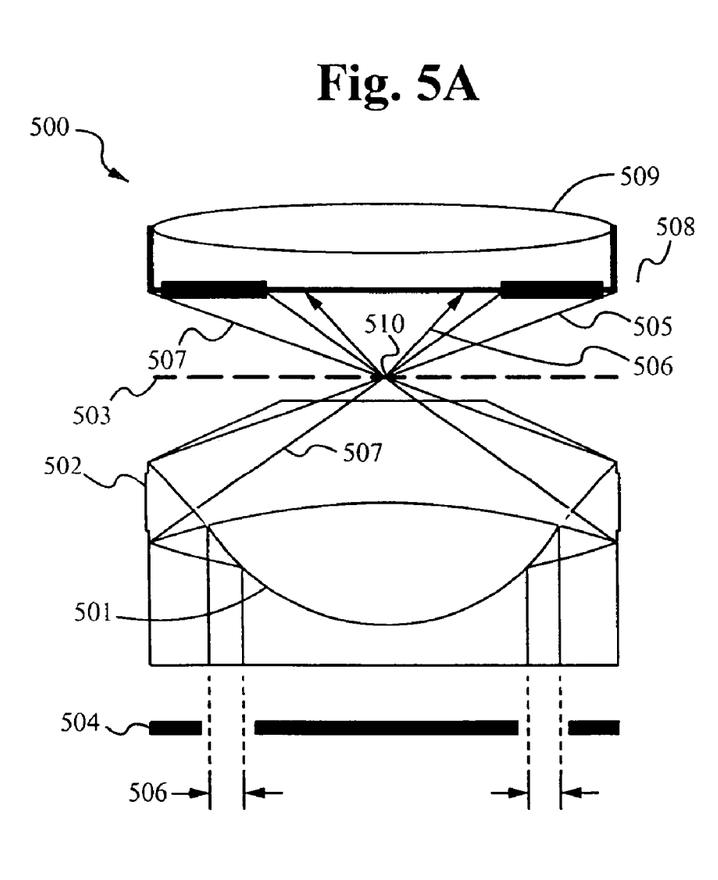
FIG. 5A is a view of the condenser with the iris in a "closed" position.
Figure 5B:
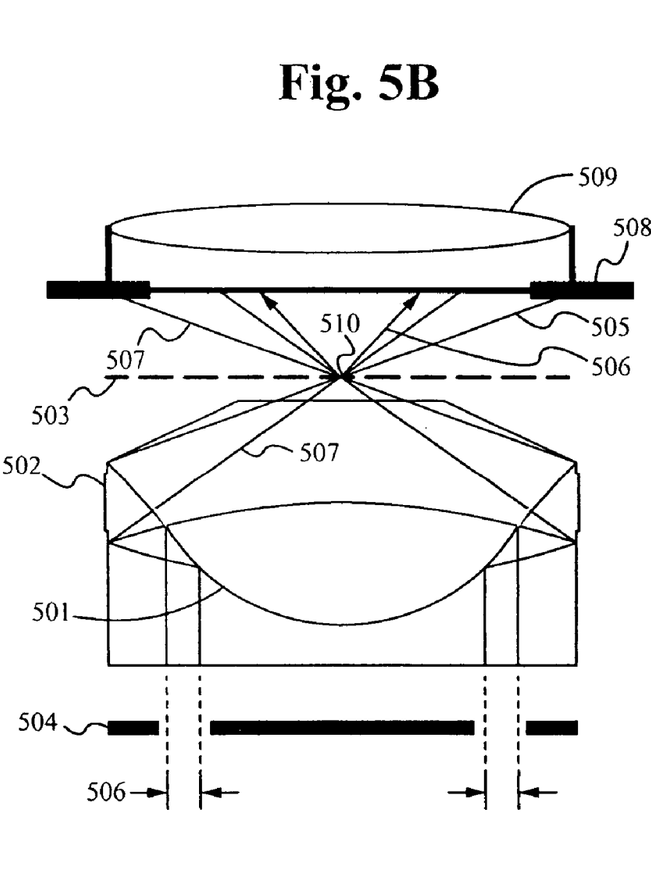
FIG. 5B is a view of the condenser with the iris in an "open" position.

FIGS. 5A and 5B show another aspect of the condenser 500 of the present invention. The iris 508 is adjustable to allow and disallow incident light 507 from reaching the objective lens 509. This allows the apparatus to be capable of both brightfield and darkfield microscopy techniques. In FIG. 5A, the iris 508 is "closed". The emitted light 506 is still able to enter the objective lens 509, however, the incident light 507 is effectively blocked. Blocking the incident light 507 achieves the necessary conditions for darkfield observation.

Alternately, in FIG. 5B, the iris 508 is "open". The emitted light 506 is still able to enter the objective lens 509, and the incident light 507 is also allowed. Allowing the incident light 507 achieves the necessary conditions for brightfield observation.

The condenser of the present invention is an integral part of the illumination system and there is no need to align it with the light source, thus eliminating the need for specially trained people to align the equipment. Further, the condenser of the present invention allows fine focusing and positioning of the focal point at any depth in the sample (not shown). In one embodiment of the present invention, the condenser is able to be adjusted up and down. This adjustment positions the focal point of illumination just below the upper surface of the sample and close to the objective lens (not shown). In this configuration, the emitted flourescent light does not pass through the entire sample before reaching the objective lens. This strategy allows sharp and intense fluorescence images, thus eliminating the likelihood that the emitted fluorescent light will pass through the sample before reaching the objective lens and therefore become partially absorbed and scattered resulting in a less intense image.

The present invention produces a very efficient separation of incident light from light that is produced as a result of fluorescence and scattering, thus eliminating the need for the excitation filter and/or barrier filter. When filters are not used and fluorochromes are present in the sample, and the present invention is fitted with a transmitted light microscope, the images produced comprise a superposition of ultra-resolution images that would have existed without fluorochromes and fluorescence images. Contrary to the Phase Contrast microscopy technique, this technique has a better resolution and no image distortions. The images produced by the present invention are similar to those produced by differential interference contrast (DIC) microscopy but they do not require a prerequisite orientation, have a better contrast and resolution, can visualize very small particles and are less expensive. Therefore, the use of simultaneous fluorescence viewing together with ultra resolution imaging (URI) is more favorable than the combination of fluorescence viewing with phase contrast and DIC microscope techniques.

Figure 6:
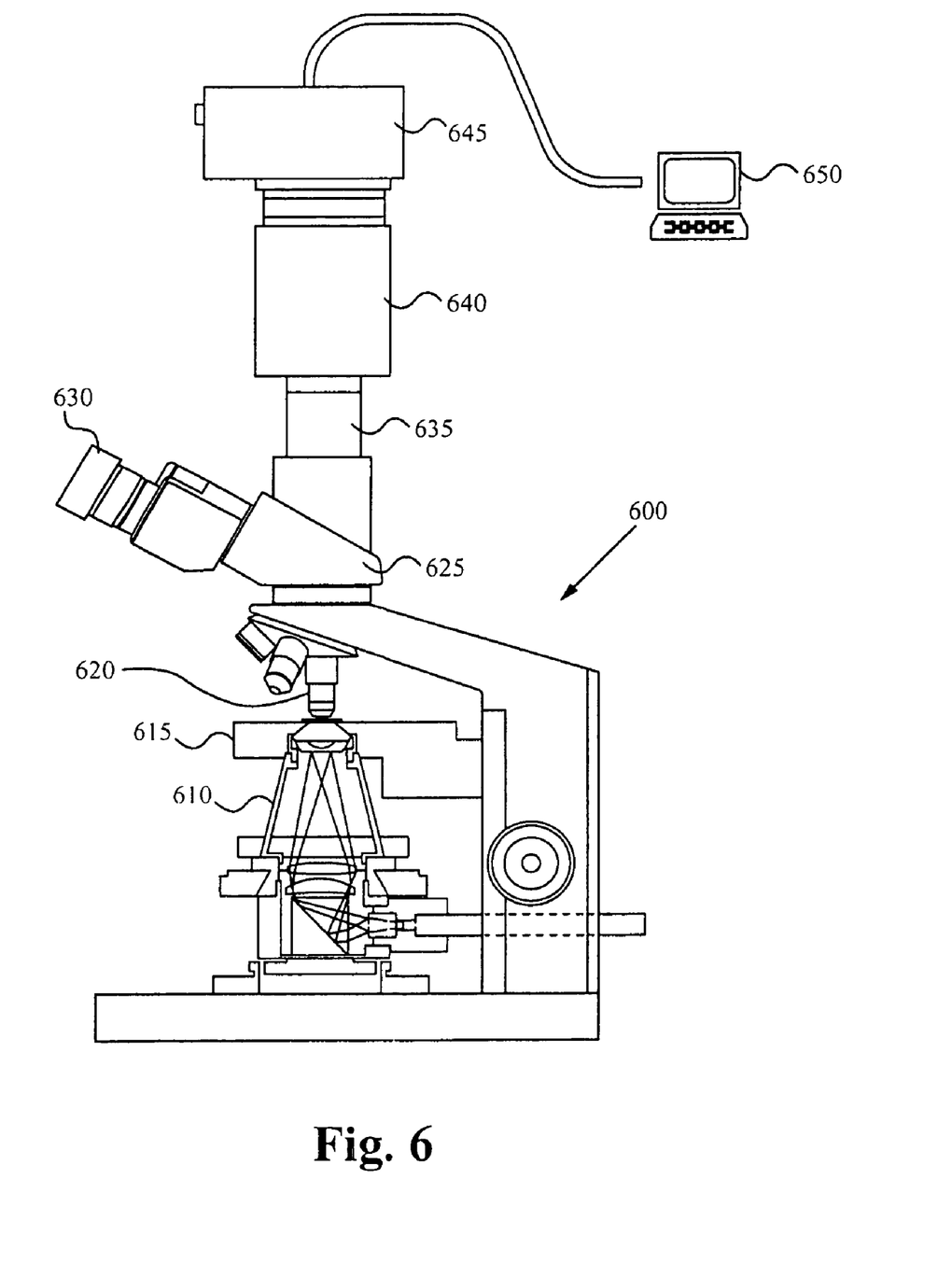
FIG. 6 is a side view of one embodiment of the present invention incorporated into a traditional research microscope.

Another embodiment of the present invention is shown in FIG. 6 which illustrates the advanced microscope illumination combined with a traditional research microscope 600. This embodiment not only eliminates the problems of conventional microscopy listed above, but also introduces new properties that make this system superior to other systems for the direct observation of living cells, cellular components and their interactions, and cell processes while they are occurring. In FIG. 6, the illumination system 610 described above is positioned under the trinocular head 625. An image is captured by an objective lens 620. Light from the objective lens 620 travels into the trinocular head 625 for viewing by an eyepiece 630 and upward through an upwardly directed projection eyepiece 635. The image is magnified by a compound relay lens 640 and transmitted to a camera 645 and a computer 650.

As shown, the improved illumination system consisting of a metal-halide lamp and an improved condenser geometry minimizes the spot size incident on the sample and reduces stray light. The condenser has a high numerical aperture (NA) which allows conditions for the creation of standing evanescent waves resulting in considerable enhancement of the microscope resolution. The present invention achieves the advantages present in both Kohler Illumination and Critical Illumination. Also, the illumination system is able to be adjusted up and down to focus the source light coming out of the condenser on the sample.

The present invention is simpler and less expensive than traditional fluorescence microscopes, has more than four times better light economy and uses considerably less power. The present invention uses a first surface mirror, has no dichroic mirror and it has an option to exclude excitation and barrier filters. The transmission efficiency of the dichroic mirror is 85% and that of the filters is 80%. The transmission efficiency of all three elements is 54.4%. Because the transmission efficiency of the first surface mirror used in the present invention, the efficiency of the present invention is at least 46% better than that of the traditional fluorescence microscope.

Furthermore, the present invention uses an inherently "cool" light. The illumination volume of the present invention can be defined by an empty light cone compared to the full light cones in traditional fluorescence microscopy, resulting in increases illumination. Also, the present invention allows for simultaneous viewing together with a Ultra Resolution Imaging (URI).

The option to not include filters provides the present invention another advantage. Using the present invention without filters allows multicolor images to be taken as a single recording. This is contrary to the conventional technique where multiple-exposure images need to be acquired using different bandpass filters appropriate for certain stains.

Finally, certain embodiments of the present invention are self-contained portable illumination devices. Other distinct usage and design advantages exist in the present invention and will be apparent to one normally skilled in the art.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications can be made in the embodiment chosen for illustration without departing from the spirit and scope of the invention. Specifically, it will be apparent to one of ordinary skill in the art that the device and method of the present invention could be implemented in several different ways and have several different appearances.

What is claimed is:

1. An illumination device for microscopes comprising:
   a metal-halide light source for producing light;
   a cardioid condenser;
   an adjustable annular diaphragm including a variable sized opening for passage of light;
   a spherical lens; and
   an iris opening;
wherein the light from the metal-halide light source enters the cardioid condenser through the variable sized opening of the annular diaphragm, wherein the spherical lens focuses the light toward the iris opening, and wherein the light exits the iris opening at an angle and comes to a focal point with a spot size and continues past the focal point producing background light.

2. The illumination device for microscopes according to claim 1, wherein the adjustable annular diaphragm, the spherical lens and the iris opening are including within the cardioid condenser.

3. The illumination device for microscopes according to claim 1, wherein the metal-halide light source further comprises:
   a metal-halide lamp;
   a light guide; and
   a collimating light adaptor,
wherein the collimating light adaptor collimates the light into a hollow cylindrical beam.

4. The illumination device for microscopes according to claim 3, wherein the collimating light adaptor is an axicone light adaptor.

5. The illumination device for microscopes according to claim 1, wherein the variable sized passage in the annular diaphragm is a cylindrical passage.

6. The illumination device for microscopes according to claim 1, wherein the angle at which light exits the iris is changed as the size of the variable sized passage in annular diaphragm is varied.

7. The illumination device for microscopes according to claim 6, wherein the variable sized opening comprises a Numerical Aperture selected from the range of 1.25 to 1.43.

8. The illumination device for microscopes according to claim 1, wherein the iris opening is adjustable to alternatively allow and retard the passage of background light.

9. An illumination device for microscopes comprising:
   a metal-halide light source for producing light;
   a collimating light adaptor; and
   a cardioid condenser, the cardioid condenser comprising:
      an adjustable annular diaphragm including a variable sized cylindrical opening for passage of light;
      a spherical lens; and
      an adjustable iris opening;

wherein collimating light adaptor collimates the light from the metal-halide light source to form a hollow cylinder of light, further wherein the hollow cylinder of light enters the cardioid condenser through the variable sized cylindrical opening, wherein the spherical lens focuses the light toward the adjustable iris opening, such that the light exits the iris opening and comes to a focal point with a spot size and continues past the focal point, producing background light, and further wherein the adjustable iris opening is adjusted to alternatively allow and retard the passage of background light.

10. The illumination device for microscopes according to claim 9, wherein the adjustable annular diaphragm is positioned at the bottom surface of the cardioid condenser.

11. The illumination device for microscopes according to claim 9, wherein the collimating light adaptor is an axicone light adaptor.

12. The illumination device for microscopes according to claim 11, wherein the variable sized opening in the bottom of the condenser is a cylindrical opening.

13. The illumination device for microscopes according to claim 11, wherein the angle at which light exits the adjustable iris opening is changed as a size of the variable sized opening in the annular diaphragm is varied.

14. The illumination device for microscopes according to claim 13, wherein the variable sized opening comprises a Numerical Aperture selected from the range of 1.25 to 1.43.

15. A direct-view light optical microscope comprising:
an illumination system including:
a metal-halide light source for producing light;
a collimating light adaptor;
a cardioid condenser, the cardioid condenser comprising:
an adjustable annular diaphragm including a variable sized opening for passage of light;
a spherical lens; and
an adjustable iris opening;
a stage with a sample; and
an objective lens;
wherein the collimating light adaptor collimates the light from the metal-halide light source to form a hollow cylinder of light, further wherein the hollow cylinder of light enters the cardioid condenser through the variable sized opening, wherein the spherical lens focuses the hollow cylinder of light toward the adjustable iris opening such that the hollow cylinder of light exits the iris opening producing incident light, wherein the incident light comes a focal point with a spot size and continues past the focal point producing background light, and wherein the adjustable iris opening is adjusted to alternatively allow and retard the passage of background light, wherein the focal point is focused on the sample, wherein the incident light excites the molecules in the sample producing fluorescent light, and further wherein the objective lens gathers fluorescent light and the allowed background light, allowing an image of the sample to be observed.

16. The direct-view light optical microscope according to claim 15, wherein the adjustable annular diaphragm is positioned at the bottom surface of the cardioid condenser.

17. The illumination device for microscopes according to claim 15, wherein the variable sized opening for passage of light is a cylindrical opening.

18. The illumination device for microscopes according to claim 15, wherein the angle at which light from the metal-halide light source exits the adjustable iris opening is changed as a size of the variable sized opening for the passage of light is varied.

19. The illumination device for microscopes according to claim 18, wherein the variable sized opening for the passage of light comprises a Numerical Aperture selected from the range of 1.25 to 1.43.

20. A method of observing living cells in a microscope comprising:
producing illumination from a metal-halide light source;
directing the illumination to a cardioid condenser;
adjusting an annular diaphragm to allow passage of illumination into the cardioid condenser, wherein the illumination is reflected by a spherical lens to an inside surface of the cardioid condenser, and further wherein the illumination is again reflected by the inside surface of the cardioid condenser through an iris opening, forming a focal point, wherein illumination continues past the focal point producing background illumination;
focusing the focal point on a sample,
adjusting the focal point to a desired depth in the sample by moving the cardioid condenser; and
observing the living cell through an observation lens.

21. The method of observing living cells according to claim 20, further comprising collimating the illumination into a hollow cylinder of light with a collimating light adaptor before the illumination is directed to the cardioid condenser.

22. The method of observing living cells according to claim 21, wherein the collimating light adaptor is an axicone light adaptor.

23. The method of observing living cells according to claim 20, wherein the iris opening is adjusted to allow passage of background light, thus producing a brightfield image.

24. The method of observing living cells according to claim 20, wherein the iris opening is adjusted to block passage of background light, thus producing a darkfield image.

25. A method of observing living cells with a direct-view light optical microscope comprising:
connecting the observation lens of a direct-view light optical microscope to a camera;
connecting the camera to a computer;
producing illumination from a metal-halide light source;
directing the illumination to a cardioid condenser;
adjusting an annular diaphragm to allow passage of illumination into the cardioid condenser, wherein the illumination is reflected by a spherical lens to an inside surface of the cardioid condenser, and further wherein the illumination is again reflected by the inside surface of the cardioid condenser through an iris opening, forming a focal point, wherein illumination continues past the focal point producing background illumination;
focusing the focal point on a sample,
adjusting the focal point to a desired depth in the sample by moving the cardioid condenser; and
obtaining an image from the observation lens through the camera;
storing the image information from the computer onto the computer; and
observing the image of the living cell with a computer.

26. The method of observing living cells with a direct-view light optical microscope according to claim 25, further comprising collimating the illumination into a hollow cylinder of light with a collimating light adaptor before the illumination is directed to the cardioid condenser.

27. The method of observing living cells with a direct-view light optical microscope according to claim 26, wherein the collimating light adaptor is an axicone light adaptor.

28. The method of observing living cells with a direct-view light optical microscope according to claim 25, wherein the iris opening is adjusted to allow passage of background light, thus producing a brightfield image.

29. The method of observing living cells with a direct-view light optical microscope according to claim 25, wherein the iris opening is adjusted to block passage of background light, thus producing a darkfield image.

* * * * *